United States Patent [19]

Hsia

[11] Patent Number: 4,587,373
[45] Date of Patent: May 6, 1986

[54] DIMETHYLETHER RECOVERY AND/OR RECYCLE IN AN MTC CONVERSION PLANT

[75] Inventor: Chung H. Hsia, Matawan, N.J.

[73] Assignee: Mobil Oil Corporation, New York, N.Y.

[21] Appl. No.: 680,712

[22] Filed: Dec. 12, 1984

[51] Int. Cl.$^4$ ............................................... C07C 1/20
[52] U.S. Cl. .................................. 585/639; 422/288; 422/289; 422/290; 585/408; 585/469; 585/640; 585/733
[58] Field of Search ............... 585/640, 408, 469, 639, 585/733, 48 M; 422/288, 289, 290

[56] References Cited

U.S. PATENT DOCUMENTS 4,387,263  6/1983  Vogt et al. ........................ 585/640

FOREIGN PATENT DOCUMENTS 0065112  5/1981  European Pat. Off. ........... 585/640
2061999  5/1981  United Kingdom .
2096604  10/1982  United Kingdom .

Primary Examiner—John Doll
Assistant Examiner—A. Pal
Attorney, Agent, or Firm—Alexander J. McKillop; Michael G. Gilman; Dennis P. Santini

[57] ABSTRACT

Disclosed is a method and apparatus for the recovery and/or recycling of dimethylether (DME) during a methanol-to-chemical (MTC) conversion reaction. The hydrocarbon output is divided into liquid, vaporous and aqueous products. The liquid hydrocarbon products are reboiled to liberate dissolved DME and then provided as a liquid hydrocarbon product output. Vapor products resulting from the reboiling are combined with the vapor hydrocarbon stream and DME is removed therefrom in a DME absorber. The resultant vaporous hydrocarbons are passed out of the system as a product and the DME absorber materials recycled. In one embodiment, the DME absorber materials are methanol and water and these are combined with the aqueous liquid stream, stripped to reduce the water content, and resubmitted to the MTC reaction section for conversion. In another embodiment, water is the only DME absorber material and it is passed to a fractionator, separating and removing the DME product from the water which is subsequently combined with the aqueous liquid stream, stripped to increase methanol, DME concentration and provided as an input to the MTC reaction section.

8 Claims, 2 Drawing Figures

DIMETHYLETHER RECOVERY AND/OR RECYCLE IN AN MTC CONVERSION PLANT

BACKGROUND OF THE INVENTION

1. Field of the Invention

The present invention relates generally to a method and apparatus for converting methanol to chemicals (MTC). More particularly, the present invention relates to an improved method and apparatus for recovering and recycling dimethylether (DME) in an MTC conversion plant.

2. Discussion of the Prior Art

Processes for making hydrocarbons from gas mixtures containing methanol, dimethylether (DME) and steam in the presence of catalysts at various temperatures and pressures are well known. U.S. Pat. No. 4,387,261 issued June 7, 1983 to Vogt et al is representative of such MTC systems, which utilize zeolite catalysts, preferably the ZSM-5 type zeolite catalysts. The primary object of the Vogt patent is the production of lower olefins ($C_2$–$C_4$) in the highest possible proportions from an input feed, comprising methanol, DME and stem. As stated in Vogt, increasing the reaction pressure is in conflict with the goal of the Vogt invention, i.e., the maximization of lower olefin production. However, a problem with low pressure operation in such plants is the physical size required to obtain a desired mass flow. At a given mass flow velocity, the pumps, pipes, towers, separators, reactors, etc., of a higher pressure system will be smaller than those of a lower pressure system. Therefore, it would be more economical to operate such an MTC system at substantially higher pressures in order to occupy the least amount of plant volume possible.

Although Vogt suggests the possibility of operating the MTC reactor at pressures of up to 10 bars, the preference would be to operate at much lower pressures in order to stimulate production of lower olefins. DME is created by the dehydration of methanol and is also consumed in the conversion to hydrocarbon process. At near atmospheric pressure, the amount of DME which would be dissolved in the liquid hydrocarbon stream 7, in the figure in Vogt, is very small and can be considered insignificant. However, as the system operating pressure is raised, as much as 20% volume of the liquid hydrocarbon stream 7 will be DME at 65 psig (approximately 4 bar). Therefore, if the product separator and reactor system were to operate at above atmospheric pressures (in order to reduce the plant volume) DME recovery will be necessary in order to maintain operating efficiency and to avoid the need for further liquid hydrocarbon processing downstream of the MTC conversion plant (to remove the unwanted dissolved DME). Because DME is one of the input chemicals consumed by the MTC reactor, the recycling of all DME through the reactor, producing a zero net DME output, will provide the highest methanol-to-chemical conversion efficiency. However, it may be desirable to obtain a portion of the DME created in the system as a product.

SUMMARY OF THE INVENTION

It is an object of the present invention to provide an improved method and apparatus for conversion of methanol to chemical, which maintains a high conversion efficiency but operates at a pressure substantially above atmospheric.

It is a further object of the present invention to provide a method and apparatus for recovering dimethylether (DME) from the hydrocarbon stream in an MTC conversion plant.

It is an additional object of the present invention to provide a method and apparatus for the recycling of DME contained in the hydrocarbon output of a MTC conversion plant.

In accordance with a method aspect of the present invention, the above and other objects are achieved wherein the products of an MTC reactor are separated into a liquid hydrocarbon stream, a vaporous hydrocarbon stream and an aqueous liquid stream, said method comprising the steps of: reboiling in a stabilizer tower said liquid hydrocarbon stream and removing the tower bottoms as a liquid hydrocarbon product stream; combining stabilizing tower overheads with the vaporous hydrocarbon stream and passing them into a DME absorber tower; removing DME absorber tower overheads as a vaporous hydrocarbon product stream; and combining DME absorber tower bottoms with said aqueous liquid stream and supplying the combination as an input to said MTC reactor.

In accordance with an apparatus aspect of the present invention, the above and other objects are achieved in an MTC conversion plant, where the hydrocarbon product stream is separated into a liquid hydrocarbon stream, a vaporous hydrocarbon stream and an aqueous liquid stream, said apparatus comprising: stabilizer means for reboiling said liquid hydrocarbon stream and for removing the bottoms as a liquid hydrocarbon product stream; DME absorber means for absorbing DME from a hydrocarbon product; means for combining overheads from said stabilizer means with said vaporous hydrocarbon stream and passing to said DME absorber means; means for removing overheads in said DME absorber means as a vaporous hydrocarbon product stream; and means for combining bottoms in said DME absorber means with said aqueous liquid stream and for providing said combined aqueous stream as an input to said MTC reactor.

BRIEF DESCRIPTION OF THE DRAWINGS

A more complete appreciation of the invention, and many of the attendant advantages thereof, will be readily apparent as the same becomes better understood by reference to the accompanying drawings, wherein.

DETAILED DESCRIPTION OF PREFERRED EMBODIMENTS

Figure 1:
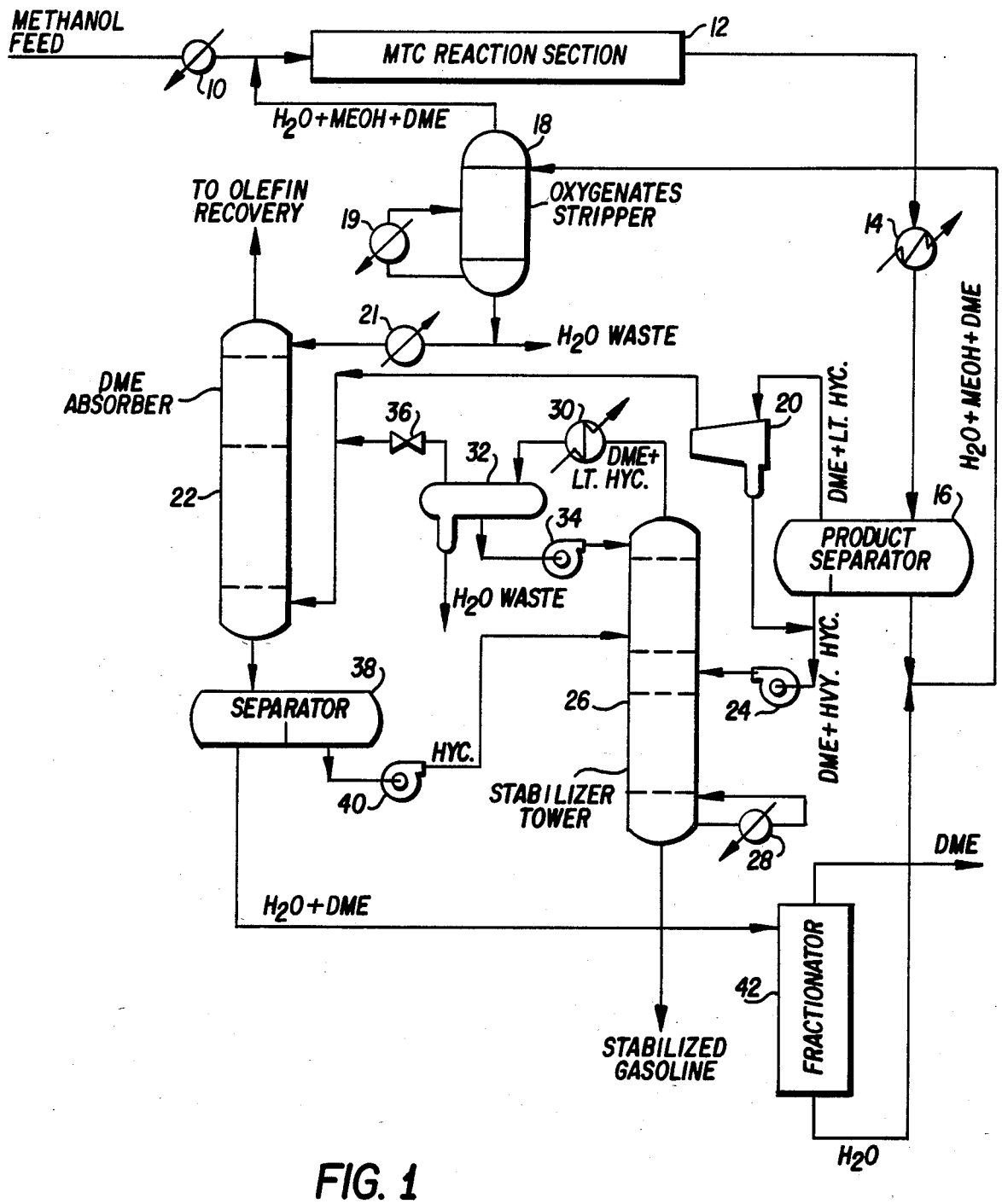
FIG. 1 is a process flow diagram of one embodiment of the present invention which provides a DME output.

Referring now more particularly to the drawings, wherein like reference numerals represent similar elements throughout the several views, FIG. 1 is a process flow diagram of a preferred embodiment of the present invention, which provides DME as a product output. A methanol feed is supplied through heater 10, is mixed with an aqueous stream comprising water, methanol and DME, and is supplied as an input to MTC reaction section 12. The MTC reaction section could be a reactor like reactor 4 described in the Vogt et al reference.

However, in a preferred embodiment, there would first be a dehydration reactor to break the methanol into a methanol/DME/water mixture and then a hydrocarbon conversion reactor to change the mixture into hydrocarbon components. It is desirable that a certain amount of water be included as an input to the MTC reaction section, because the conversion of methanol to hydrocarbons over zeolite catalysts is an exothermic reaction, and water, in changing state from liquid to steam, serves to absorb excess heat.

The hydrocarbon stream output from the MTC reaction section 12 is passed through liquid cooled heat exchanger 14 and is supplied as an input to product separator 16. In a preferred embodiment, the product separator is maintained at about 65 psig and around 100° F. The separator serves to separate vaporous hydrocarbons from the other liquids and serves to separate liquid hydrocarbons from aqueous liquids contained therein. An aqueous stream, comprising water, methanol and DME, is removed from the product separator and passed to an oxygenates stripper 18. The oxygenates stripper 18 includes reboiler 19 and provides, as an overhead, a higher concentration of methanol and DME in an aqueous solution, which is combined with the input methanol feed as an input to the MTC reaction section 12. The excess water removed can be either discarded as waste or utilized by a DME absorber tower.

Because the major portion of any DME in the oxygenates stripper overhead is recycled into the input of the MTC reaction section 12, no DME will be wasted and it can be completely reacted. However, additional DME is dissolved, both in the vaporous hydrocarbon streams and liquid hydrocarbon streams which exit the product separator 16. The vaporous hydrocarbon stream, comprising mainly light hydrocarbons and DME, is compressed in compressor 20, with any condensate passing back into the liquid hydrocarbon stream output of product separator 16. The compressed vaporous hydrocarbon stream is passed into the DME absorber.

The liquid hydrocarbon stream, containing DME and heavy hydrocarbons, is transferred to injection pump 24 into stabilizer tower 26 which in a preferred embodiment has an internal pressure of around 300 psig. The heavy hydrocarbon bottoms are reboiled by means of heat exchanger 28, liberating any DME or light hydrocarbon varpors dissolved therein. The resultant stabilized heavy hydrocarbons, comprising higher aliphates and aromates in the gasoline boiling range, are removed as a stabilized gasoline product which would need no additional treatment.

The overhead vaporous products, comprising DME and previously dissolved light hydrocarbon vapors, are cooled in liquid cooled heat exchanger 30 and provided to separator 32, whereupon condensed water is removed as a waste product and any condensed hydrocarbon materials are resubmitted to stabilizer tower 26 by means of injection pump 34. The remaining DME and light hydrocarbon vapors pass from separator 32 through a control valve 36, are combined with the DME and light hydrocarbon vapors from compressor 20, and are input to the DME absorber 22 at a lower portion thereof.

Water is supplied to the DME absorber 22 by oxygenates stripper 18 through cooler 21 and travels countercurrent with respect to the light hydrocarbon and DME vapors in the absorber tower. This flow of water serves to absorb DME without absorbing the light hydrocarbons. The light hydrocarbon overheads pass out of the tower as a recovered olefin product and the scrubbing water, with dissolved DME, is removed as an absorber tower bottom product. In the preferred embodiment, the absorber tower operates at around 150 psig and 100° F. DME absorber bottoms are provided to separator 38, where any remaining liquid hydrocarbons are passed through injection pump 40 and resubmitted to stabilizer tower 26. The wash water, with DME dissolved therein, is passed to fractionator 42 which separates DME from water.

The DME output from fractionator 42 can comprise an output product, whereas the water can be added to the aqueous liquid stream from product separator 16 and recycled through the MTC reaction section 12. It can be seen, in FIG. 1, that the only DME output from the system is the DME output of fractionator 42, and not through DME dissolved in the light or heavy hydrocarbon products (olefins and gasoline, respectively).

As noted previously, where it is not desirable to produce a net DME output, the DME can be an advantageous input product to the MTC reaction section 12. Because there is no net DME output, the DME would be reacted to extinction by recycling through the MTC reaction section. Several minor changes in the process flow diagram would result if no net DME output were desired. By reference to FIG. 2, a process flow diagram for such a non-DME producing conversion plant is illustrated. The product separator 16, oxygenates stripper 18, stabilizer tower 26, DME absorber 22 and the other components illustrated operate in precisely the same manner as previously discussed with reference to FIG. 1. The aqueous output of separator 38 does not go to a fractionator, as in FIG. 1, and instead is combined with the aqueous liquid output of produce separator 16 and recycled through oxygenates stripper 18. Because the DME is harder to separate from methanol than from water, where it is desirable to recover DME, in FIG. 1, only water is used in the DME absorber allowing simple fractionation to separate the DME and water.

Figure 2:
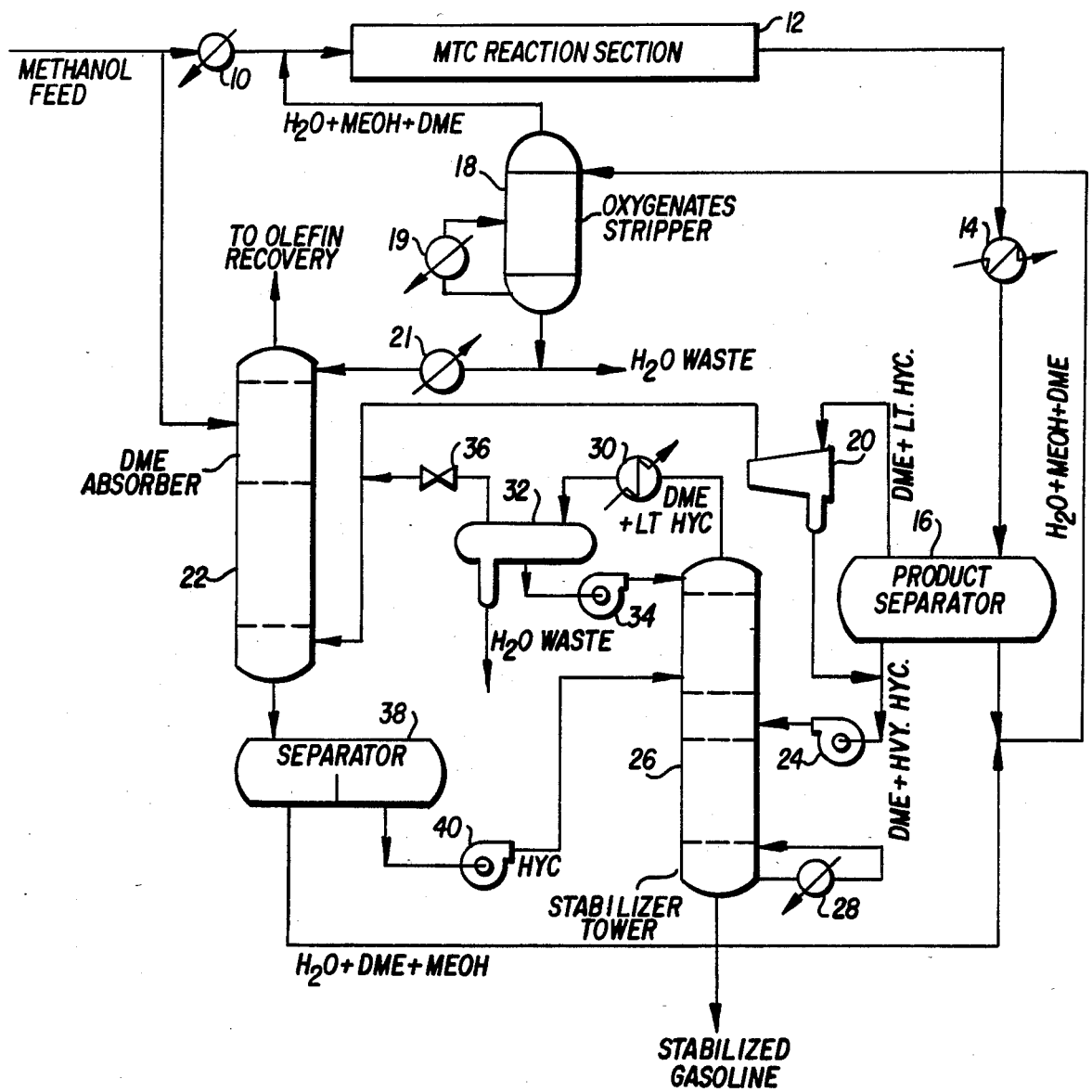
FIG. 2 is a process flow diagram of a further embodiment of the present invention which provides no net DME output.

Where, as in FIG. 2, the DME is to be recycled to extinction through the MTC reaction section, its greater affinity for methanol can be utilized to reduce the water and thus size requirements of the DME absorber 22. Consequently, a portion of the methanol feed is directed into DME absorber 22, improving its efficiency, allowing a smaller absorber to achieve the same absorption efficiency as the DME absorber in FIG. 1. However, the aqueous solution separated from hydrocarbons in separator 38 comprises not only water and DME, but also methanol as a bottom product of the DME absorber 22. It is this water/DME/methanol separator output which is combined with the product separator aqueous output and recycled through oxygenates stripper 18 to the MTC reaction section 12. Thus, in the FIG. 2 embodiment, the same light and heavy hydrocarbon outputs are provided, free from DME contamination, but no net DME is provided by the system.

In both embodiments shown in FIGS. 1 and 2, the overall MTC conversion plant size can be substantially reduced because of the above atmospheric operating pressures, without compromising the efficiency of the conversion process (in reacting all DME) and providing uncontaminated (by DME) output hydrocarbon products.

In view of the above disclosure, many modifications and variations on the method steps and apparatus disclosed in FIGS. 1 and 2 will be obvious to those of ordinary skill in the methanol-to-chemical conversion art. The primary benefit of the present invention, a more compact MTC processing plant, is achieved when operating at pressures substantially above atmospheric. It is anticipated that a range of separator pressures of from 3 to 20 bar will be compatible with the present system. Therefore, the present invention is not limited by the above disclosure, and is limited only by the scope of the claims attached hereto.

The embodiments of the invention in which an exclusive property or privilege is claimed are defined as follows:

1. A process for recovering DME from the product stream exiting an MTC reactor, wherein said product stream is separated into a liquid hydrocarbon stream, a vaporous hydrocarbon stream and an aqueous liquid stream, both hydrocarbon streams including dissolved DME, said process comprising the steps of:

reboiling said liquid hydrocarbon stream at least to remove dissolved DME in a stabilizer tower and removing bottoms of said stabilizer tower as a liquid hydrocarbon product stream;

combining overheads of said stabilizer tower comprising said at least DME removed from said liquid hydrocarbon stream with said vaporous hydrocarbon stream to form a first combination and passing the first combination to a DME absorber tower;

absorbing DME from said first combination in said absorber tower;

removing overheads from the DME absorber tower as a vaporous hydrocarbon product; and combining at least a portion of DME absorber tower bottoms with said aqueous liquid stream to form a second combination and recycling said second combination as an input to said MTC reactor.

2. The process according to claim 1, wherein in conjunction with said reboiling step, there is provided the further step of compressing said vaporous hydrocarbon stream and passing any resultant condensate to said liquid hydrocarbon stream and passing the remaining compressed vapors as said vaporous hydrocarbon stream for combination with said stabilizer tower overheads in said first combining step.

3. The process according to claim 1, wherein said absorbing step includes the injection of methanol feed into said DME absorber tower and said second combining step includes passing said second combination of DME absorber tower bottoms and said aqueous liquid stream to an oxygenates stripper for improving the concentration of methanol and DME in aqueous solution before recycling in said MTC reaction section.

4. The method according to claim 1, wherein immediately before said second combining step there is the further step of fractionating said DME absorber tower bottoms, and providing a DME product output, and said second combining step includes combining fractionator bottoms with said aqueous liquid stream and supplying said combination to an oxygenates stripper for improving the concentration of said DME and methanol components in aqueous solution before recycling in said MTC reaction section.

5. An apparatus for recovering DME from the product stream exiting an MTC reactor, wherein said product stream is separated into a liquid hydrocarbon stream, a vaporous hydrocarbon stream and an aqueous liquid stream, said apparatus comprising:

stabilizer tower means for reboiling said liquid hydrocarbon stream and removing DME dissolved in said liquid hydrocarbon stream creating tower overheads and tower bottoms, said stabilizer tower bottoms comprising said liquid hydrocarbon product stream;

DME absorber means for absorbing DME from an input, said DME absorbing means providing overheads and bottoms as products therefrom;

first means for combining said stabilizer tower overheads including said removed DME with said vaporous hydrocarbon stream to produce a first combination and passing said first combination as an input to said DME absorbing means, wherein said DME absorber overheads comprise a vaporous hydrocarbon product; and second meas for combining at least a portion of said DME absorber bottoms with said aqueous liquid stream to produce a second combination and for recycling said second combination as an input to said MTC reactor.

6. The apparatus according to claim 5, further including:

means for compressing said vaporous hydrocarbon stream, for passing any resultant condensate to said liquid hydrocarbon stream, and for passing remaining compressed vapors to said first combining means.

7. The apparatus according to claim 5, further including means for injecting methanol feed into said DME absorber means; and oxygenate stripper means for improving the concentration of methanol and DME in said second combination as an input to said MTC reactor.

8. The apparatus according to claim 5, further comprising:

fractionating means for fractionating DME absorber bottoms, said fractionating means providing a DME product output and bottoms, wherein said second combining means combines said fractionating means bottoms with said aqueous liquid stream to form said second combination; and oxygenates stripper means for improving the concentration of methanol and DME in said second combination before recycling in said MTC reaction section.

* * * * *

UNITED STATES PATENT AND TRADEMARK OFFICE
CERTIFICATE OF CORRECTION

PATENT NO. : 4,587,373

DATED : May 6, 1986

INVENTOR(S) : Chung Hweng Hsia

It is certified that error appears in the above-identified patent and that said Letters Patent is hereby corrected as shown below:

Column 1, line 25, "stem" should be --steam--

Column 3, line 43, "to" should be --by--

Column 4, line 36, "produce" should be --product--

Column 6, line 27, "meas" should be --means--

Signed and Sealed this

Tenth Day of February, 1987

Attest:

DONALD J. QUIGG

Attesting Officer

Commissioner of Patents and Trademarks